United States Patent [19]

Vora et al.

[11] Patent Number: 4,869,808

[45] Date of Patent: * Sep. 26, 1989

[54] HYDROCARBON CONVERSION PROCESS WITH RADIAL FLOW AND CONTROLLED HYDROGEN ADDITION

[75] Inventors: Bipin V. Vora, Darien; Norman H. Scott, Arlington Heights, both of Ill.

[73] Assignee: UOP, Des Plaines, Ill.

[*] Notice: The portion of the term of this patent subsequent to Jan. 19, 2005 has been disclaimed.

[21] Appl. No.: 176,574

[22] Filed: Apr. 1, 1988

[51] Int. Cl.$^4$ .................. C10G 23/00; C10G 35/00
[52] U.S. Cl. ........................... 208/138; 208/143; 208/146; 208/166; 208/169; 208/DIG. 1; 585/660
[58] Field of Search ............... 208/138, 139, 143, 146, 208/46, DIG. 1, 166, 169; 585/444, 627, 660

[56] References Cited

U.S. PATENT DOCUMENTS

| | | | |
|---|---|---|---|
| 2,646,391 | 7/1953 | Houdry | 208/146 X |
| 2,683,654 | 7/1954 | Bergman | 23/288 |
| 3,692,496 | 9/1972 | Greenwood et al. | 23/288 G |
| 3,706,536 | 12/1972 | Greenwood et al. | 23/288 G |
| 3,725,248 | 4/1973 | Greenwood et al. | 208/138 |
| 3,882,015 | 5/1975 | Carson | 208/169 |
| 3,907,605 | 9/1975 | Winter, III et al. | 208/146 |
| 4,374,094 | 2/1983 | Farnham | 208/146 X |
| 4,720,336 | 1/1988 | Vora et al. | 208/46 |

Primary Examiner—Glenn Caldarola
Attorney, Agent, or Firm—Thomas K. McBride; John G. Tolomei; John G. Cutts, Jr.

[57] ABSTRACT

A continuous process for hydrocarbon conversion wherein a hydrocarbon charge stock is catlytically converted in the presence of hydrogen at hydrocarbon conversion conditions including a first inlet temperature, a first hydrogen to hydrocarbon mole ratio and a first mass flow rate of hydrocarbon into a hydrocarbon product stream in a high space velocity moving bed radial flow reactor containing catalyst wherein at least a portion of the catalyst is pinned and thereby immobilized during high space velocity conversion which process comprises: (a) reducing the first inlet temperature of the reactor by about 10° F. (5.5° C.) to about 100° F. (55.5° C.) to a second inlet temperature thereby lowering the rate of the hydrocarbon conversion; (b) reducing the first hydrogen to hydrocarbon mole ratio to a second hydrogen to hydrocarbon mole ratio which is from about 10% to about 60% of the first hydrogen to hydrocarbon mole ratio and sufficient to unpin the catalyst from the reactor thereby ensuring uniform gravitational catalyst flow through the reactor while maintaining the first mass flow rate of hydrocarbon; (c) introducing a quantity of fresh catalyst into an upper portion of the reactor while removing a similar quantity of spent catalyst from a lower portion of the reactor; (d) increasing the second hydrogen to hydrocarbon mole ratio to essentially the first hydrogen to hydrocarbon mole ratio; and (e) increasing the second inlet temperature to essentially restore the hydrocarbon conversion.

23 Claims, 1 Drawing Sheet

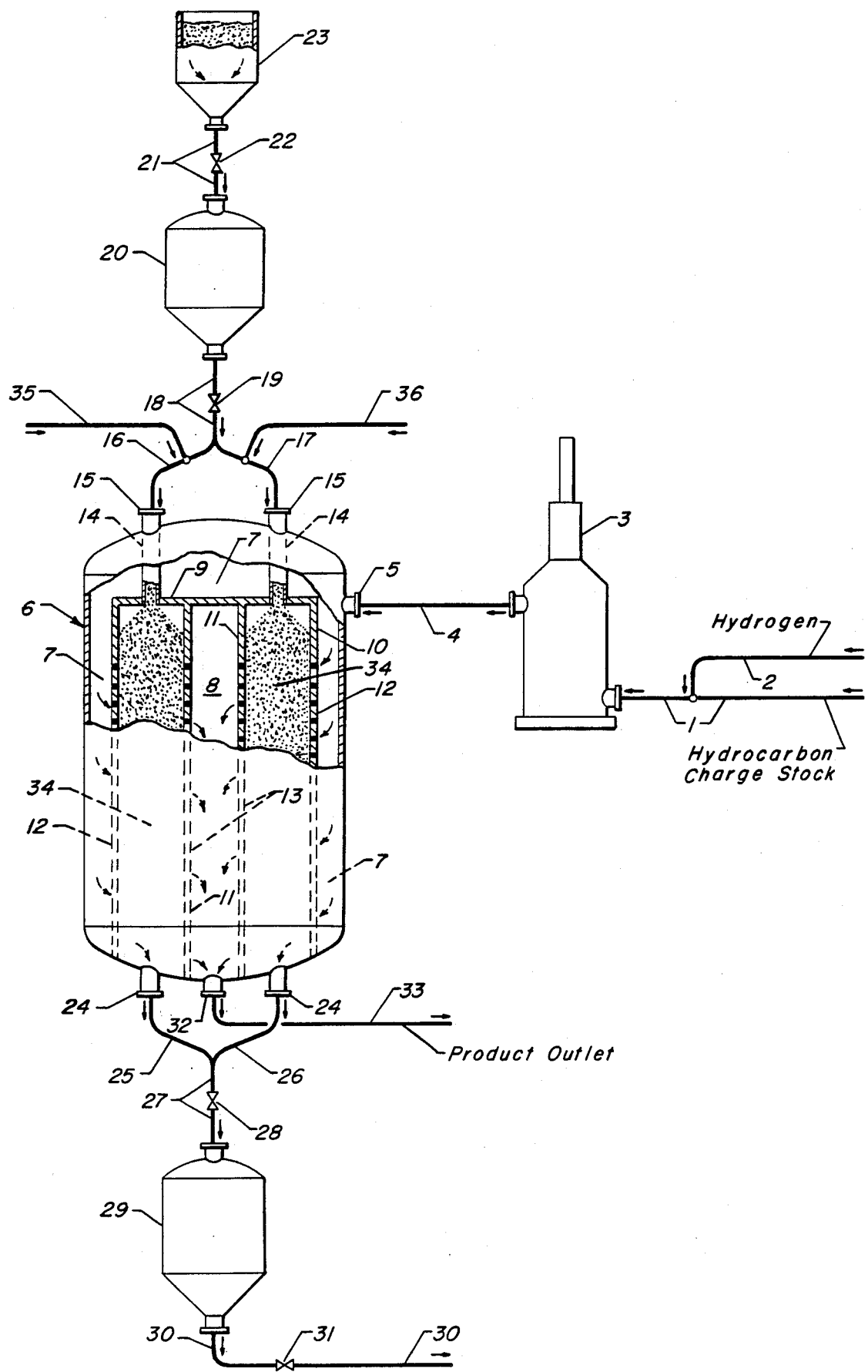

HYDROCARBON CONVERSION PROCESS WITH RADIAL FLOW AND CONTROLLED HYDROGEN ADDITION

FIELD OF THE INVENTION

The invention relates to a hydrocarbon conversion process which is useful in the vapor phase conversion of various hydrocarbon feedstocks. In particular, the present invention pertains to a process which facilitates hydrocarbon conversion wherein the conversion is preferably conducted at a high space velocity in a radial flow manner. More specifically, the invention relates to a continuous process for hydrocarbon conversion wherein a hydrocarbon charge stock is catalytically converted in the presence of hydrogen at hydrocarbon conversion conditions including a first inlet temperature, a first hydrogen to hydrocarbon mole ratio and a first mass flow rate of hydrocarbon into a hydrocarbon product stream in a high space velocity moving bed radial flow reactor containing catalyst wherein at least a portion of the catalyst is pinned and thereby immobilized during high space velocity conversion which process comprises: (a) reducing the first inlet temperature of the reactor by about 10° F. (5.5° C.) to about 100° F. (55.5° C.) to a second inlet temperature thereby lowering the rate of the hydrocarbon conversion; (b) reducing the first hydrogen to hydrocarbon mole ratio to a second hydrogen to hydrocarbon mole ratio which is from about 10% to about 60% of the first hydrogen to hydrocarbon mole ratio and sufficient to unpin the catalyst from the reactor thereby ensuring uniform gravitational catalyst flow through the reactor while maintaining the first mass flow rate of hydrocarbon; (c) introducing a quantity of fresh catalyst into an upper portion of the reactor while removing a similar quantity of spent catalyst from a lower portion of the reactor; (d) increasing the second hydrogen to hydrocarbon mole ratio to essentially the first hydrogen to hydrocarbon mole ratio; and (e) increasing the second inlet temperature to essentially restore the hydrocarbon conversion.

INFORMATION DISCLOSURE

Various vapor phase conversion processes have heretofore been effected utilizing a reactor system wherein a reactant stream is processed in radial flow through a vertically positioned annular-form catalyst bed—an arrangement that offers many design and operating advantages, particularly with respect to those vapor phase processes for the conversion of hydrocarbons. Illustrative of a reactor system wherein a reactant stream is caused to flow laterally and radially through an annular-form catalyst bed is that described in U.S. Pat. No. 2,683,654. The reactor system illustrated is intended for a fixed bed operation. A reactant stream charged to a reaction chamber flows from an outer annular-form space created between the chamber walls and the annular-form catalyst bed, said stream flowing laterally and radially through said catalyst bed and into a perforated center pipe to be discharged from the reaction chamber.

U.S. Pat. No. 3,692,496 describes a somewhat related reactor system in that a reactant stream charged to a reaction chamber is caused to flow laterally and radially from an outer annular-form space through an annular-form catalyst section and into an inner or center manifold to be discharged from said chamber. In the latter case, the reactor system comprises stacked reaction chambers (and consequently stacked annular-form catalyst sections) designed to process catalyst particles downwardly via gravity flow from one annular-form catalyst section through the next lower annular-form catalyst section, the catalyst particles being recovered from the lowermost reaction chamber for regeneration. A variation of the last described reactor system appears in U.S. Pat. No. 3,725,248 wherein the annular-form catalyst sections are individually contained in side-by-side reaction chambers, and in U.S. Pat. No. 3,882,015 wherein the reactant stream is reversed to flow laterally and radially from a center reactant conduit through an annular-form catalyst section and into an outer annular-form space formed by the annular-form catalyst section and the reaction chamber walls.

U.S. Pat. No. 3,706,536 discloses a reactor wherein the reactants flow laterally and radially across an annular-form moving catalyst bed. This patent is pertinent for its teaching that cylinder form baffle plates placed adjacent to each concentric catalyst-retaining screen to accommodate varying height catalyst beds in the annular-form catalyst section.

U.S. Pat. No. 4,720,336 discloses a catalytic reactor system and process for effecting the contact of a reactant stream with catalyst particles that are movable by gravity flow through the system.

The foregoing reactor systems and associated processes have heretofore been described with respect to vapor phase conversion processes wherein they are employed to effect a number of catalyst-promoted conversions. Prominent among such conversion processes are the hydrocarbon conversion processes and include catalytic reforming, hydrogenation, hydrocracking, hydrorefining, isomerization, and dehydrogenation, as well as alkylation, transalkylation, steam reforming, and the like. The reactor system of the present invention can be similarly employed but is of particular advantage with respect to high space velocity operation, such as hydrocarbon dehydrogenation at near-atmospheric pressures.

The present invention provides a novel process to be employed in the conversion of hydrocarbons while utilizing reaction conditions which include high linear mass velocity perpendicular (radial) to the direction of catalyst movement through the bed. Utilization of this process results in the ability to operate a hydrocarbon conversion process at conditions which restrict the movement or flow of catalyst (pinning) and hold the catalyst against the catalyst-retaining screen and yet still change the catalyst inventory in the reactor without totally discontinuing the hydrocarbon conversion operation.

BRIEF SUMMARY OF THE INVENTION

The process of the present invention provides for the continuous conversion of a hydrocarbon charge stock in a catalytic reaction zone in the presence of hydrogen at hydrocarbon conversion conditions.

A preferred embodiment of the present invention may be characterized as a continuous process for hydrocarbon conversion wherein a hydrocarbon charge stock is catalytically converted in the presence of hydrogen at hydrocarbon conversion conditions including a first inlet temperature, a first hydrogen to hydrocarbon mole ratio and a first mass flow rate of hydrocarbon into a hydrocarbon product stream in a high space velocity moving bed radial flow reactor containing catalyst wherein at least a portion of the catalyst is pinned and thereby immobilized during high space velocity conversion which process comprises: (a) reducing the first inlet temperature of the reactor by about 10° F. (5.5° C.) to about 100° F. (55.5° C.) to a second inlet temperature thereby lowering the rate of the hydrocarbon conversion; (b) reducing the first hydrogen to hydrocarbon mole ratio to a second hydrogen to hydrocarbon mole ratio which is from about 10% to about 60% of the first hydrogen to hydrocarbon mole ratio and sufficient to unpin the catalyst from the reactor thereby ensuring uniform gravitational catalyst flow through the reactor while maintaining the first mass flow rate of hydrocarbon; (c) introducing a quantity of fresh catalyst into an upper portion of the reactor while removing a similar quantity of spent catalyst from a lower portion of the reactor; (d) increasing the second hydrogen to hydrocarbon mole ratio to essentially the first hydrogen to hydrocarbon mole ratio; and (e) increasing the second inlet temperature to essentially restore the hydrocarbon conversion.

Another preferred embodiment of the present invention may be characterized as a continuous process for hydrocarbon conversion wherein a hydrocarbon charge stock is catalytically converted in the presence of hydrogen at hydrocarbon conversion conditions including a first inlet temperature, a first hydrogen to hydrocarbon mole ratio and a first mass flow rate of hydrocarbon into a hydrocarbon product stream in a high space velocity moving bed radial flow reactor containing catalyst wherein at least a portion of the catalyst is pinned and thereby immobilized during high space velocity conversion which process comprises: (a) reducing the first inlet temperature of the reactor by about 10° F. (5.5° C.) to about 100° F. (55.5° C.) to a second inlet temperature thereby lowering the rate of the hydrocarbon conversion; (b) reducing the first mass flow rate of hydrocarbon to a second mass flow rate of hydrocarbon while maintaining a second hydrogen to hydrocarbon mole ratio from about 10% to about 60% of the first hydrogen to hydrocarbon mole ratio which is sufficient to unpin the catalyst from the reactor thereby ensuring uniform gravitational catalyst flow through the reactor; (c) introducing a quantity of fresh catalyst into an upper portion of the reactor while removing a similar quantity of spent catalyst from a lower portion of the reactor; (d) increasing the second mass flow rate of hydrocarbon to essentially the first mass flow rate of hydrocarbon; (e) increasing the second hydrogen to hydrocarbon mole ratio to essentially the first hydrogen to hydrocarbon mole ratio; and (f) increasing the second inlet temperature to essentially restore the hydrocarbon conversion.

Other embodiments of the present invention encompass further details such as mechanical components, design details and apparatus for the operation of the process of the present invention, preferred operating conditions and catalysts, all of which are hereinafter disclosed in the following discussion of each of these facets of the invention.

BRIEF DESCRIPTION OF THE DRAWING

The drawing is presented in illustration of a suitable apparatus which may be used to practice the process of the present invention and is not intended as an undue limitation on the generally broad scope of the invention as set out in the appended claims. The drawing represents a side view of a reactor system which may be used in accordance with the present invention and which view is partially broken away and sectioned.

DETAILED DESCRIPTION OF THE INVENTION

As illustrated in the drawing, a hydrocarbon charge stock is provided via conduit 1 and admixed with a hydrogen-rich stream which is introduced via conduit 2 and introduced into charge heater 3 where the reactants are heated to a suitable hydrocarbon conversion temperature. The heated reactants are removed from charge heater 3 via conduit 4 and introduced into reaction chamber 6 via reactant inlet port 5. A product stream is removed from reaction chamber 6 via product outlet port 32 and conduit 33.

As further illustrated in the drawing, the apparatus comprises reaction chamber 6 which is an elongated vertically oriented chamber. At the upper end of reaction chamber 6 is catalyst storage vessel 23 which is capable of being emptied in order to transfer fresh, either new or regenerated, catalyst particles via conduit 21 and valve 22 into catalyst loading chamber 20. In the appropriate sequence, the fresh catalyst particles which have been previously loaded are permitted to gravitationally flow from catalyst loading chamber 20 via conduit 18, valve 19 and conduits 16 and 17 and through catalyst inlet ports 15 into reaction chamber 6 via catalyst conduits 14.

Reaction chamber 6 is provided with upper spaced concentric imperforate screen members 10 and 11, respectively, and lower spaced concentric perforate screen members 12 and 13, respectively, to thereby define an annular-form catalyst-retaining section 34 and cylinder center pipe volume 8. It will also be noted that there is an outer annular-form void space 7 around the full height of the outer concentric screen members 10 and 12 whereby there is a resulting flow of the reactant stream passing from reactant inlet port 5 and into void space 7 and a radial inward flow through perforate screen member 12. Imperforate screen member 10 serves to prevent the flow of the reactant stream into the upper end portion of catalyst-retaining section 34 and thereby precluding the contact of the reactant stream with the catalyst until it has gravitationally flowed to the lower end portion of catalyst-retaining section 34 which is defined by perforate screen members 12 and 13. In order to preclude the by-passing of the reactant stream from void space 7, there is transverse partition 9 over the upper end portion of catalyst-retaining section 34 and cylindrical center pipe volume 8. In addition to transverse partition 9, cylindrical center pipe volume 8 is defined by inner concentric screen members 11 and 13. Cylindrical center pipe volume 8 serves to collect the converted reactants after passage through the lower end of catalyst-retaining section 34 and then conducts the converted reactants to product outlet port 32 from which a product stream is removed from reaction chamber 6 via conduit 33.

At the desired intervals, the fresh catalyst particles gravitate downwardly through catalyst conduits 14 and into the upper end portion of catalyst-retaining section 34 and simultaneously, spent catalyst particles gravitate downwardly from the lower end portion of catalyst-retaining section 34 via catalyst outlet ports 24, conduits 25, 26 and 27, and valve 28 into catalyst collector hopper 29. After valve 28 has been closed to isolate reaction chamber 6 and at the convenience of the operator, the spent catalyst particles are then removed from catalyst collector hopper 29 via conduit 30 and valve 31.

A hydrogen-rich gas is introduced into the upper portion of annular-form catalyst-retaining section 34 via conduits 35 and 36 in conjunction with catalyst conduits 14. The introduction of a hydrogen-rich gas via conduits 35 and 36 is employed when it is desired to reduce the fresh catalyst before contact with the hydrocarbonaceous charge stock. This flow of the hydrogen-rich gas may be a continuous or intermittent addition and the flow volume is relatively small and is preferably less than about 10% of the total hydrogen-rich gas introduced into reaction chamber 6.

While the drawing depicts a sequential flow of hydrocarbon reactants into an inlet port at an upper portion of the reaction chamber, through an outer annular-form void space, through (in a radially inward fashion) perforate screen members containing catalyst, into cylindrical center pipe volume and finally through a product outlet port located in a lower portion of the reaction chamber, it is understood that the flow of the hydrocarbon stream may be reversed so that the hydrocarbon reactant inlet is at the lower portion of the reaction chamber and that the product outlet port is at the upper portion of the reaction chamber.

The reactor system herein described is of particular advantage with respect to the conversion of hydrocarbons and, in particular, the dehydrogenation of hydrocarbons in the presence of a dehydrogenation catalyst—an established and well-known hydrocarbon conversion process in the petroleum refining industry. This reactor system offers special advantages when the hydrocarbon charge stock to be dehydrogenated comprises $C_2+$ normally gaseous hydrocarbons with the desired product comprising the corresponding monoolefins. The monoolefinic products are generally useful as intermediates in the production of other more valuable products, and the catalytic dehydrogenation process is typically utilized in conjunction with various other hydrocarbon conversion processes to yield a desired final product. For example, utilizing liquid petroleum gas (LPG)—a compressed or liquefied gas consisting of propane and butane or mixed butane—as a starting material, catalytic dehydrogenation can be utilized to produce propylene and/or butylene in conjunction with an HF alkylation unit wherein said olefins are alkylated with isobutane to produce a high octane motor fuel; or in conjunction with a catalytic condensation unit wherein said olefins are condensed to form tetramers or polymer gasoline; or in conjunction with an etherification unit wherein isobutylene is reacted with methanol to produce methyl t-butyl ether, a highly desirable gasoline additive. Also, for example, the dehydrogenation of $C_{10}$–$C_{14}$ linear paraffins to $C_{10}$–$C_{14}$ linear olefins which upon subsequent alkylation with benzene produces linear alkylbenzenes which are a valuable biodegradable detergent raw material. In addition, any other desired hydrocarbon which may be vaporized can be utilized as a charge stock to a dehydrogenation process.

A catalytic dehydrogenation process will preferably utilize a catalytic composite comprising a platinum group metal component, a tin component, and an alkali metal component composited with a porous, high surface area, adsorbent support or carrier material. Of the platinum group metals, i.e., platinum, palladium, ruthenium, rhodium, osmium and iridium, platinum is a preferred catalyst component. The platinum component will generally comprise from about 0.01 to about 2.0 wt. % of the catalytic composite, and the tin component will generally comprise from about 0.1 to about 5 wt. % thereof. Of the alkali metals, i.e., cesium, rubidium, potassium, sodium, and lithium, lithium and/or potassium are preferred. The alkali metal will generally constitute from about 0.1 to about 3.5 wt. % of the catalytic composite. One preferred catalytic composite comprises from about 0.1 to about 1 wt. % platinum, and from about 0.1 to about 1 wt. % tin and from about 0.2 to about 3 wt. % lithium or potassium composited with a porous adsorbent support or carrier material having a surface area of from about 25 to about 500 m$^2$/g. The preferred carrier materials are the refractory inorganic oxides with best results being obtained with an alumina support or carrier material.

The catalytic dehydrogenation process herein contemplated is a relatively high temperature operation effected at a temperature of from about 700° F. (371° C.) to about 1400° F. (760° C.), and preferably from about 850° F. (454° C.) to about 1300° F. (704° C.). The process is also a relatively low pressure operation effected at a pressure of from subatmospheric to about 50 psig (345 kPa gauge), preferably from about 5 psig (34.5 kPa gauge) to about 30 psig (207 kPa gauge). Notwithstanding that the catalytic dehydrogenation process involves hydrogen-producing reactions, it has been the practice to charge hydrogen to the reaction zone, typically recycle hydrogen, in admixture with the hydrocarbon feedstock—a practice which has been found to promote catalyst activity as well as stability. Dehydrogenation conditions thus further include a hydrogen to hydrocarbon mole ratio from about 0.5 to about 10, and more preferably from about 1 to 6. Additionally, the catalytic dehydrogenation process is preferably conducted at relatively high liquid hourly space velocity so that the reactants have minimal exposure to thermal conversion conditions prior to contact with the dehydrogenation catalyst to substantially obviate conversion to other than the desired dehydrogenation products, that the reactants are not overly-converted when they are contacted with the modern high activity dehydrogenation catalysts which are available and that the resulting dehydrogenation products are not subjected to an inordinate heat-soak before exiting from the dehydrogenation zone. Catalytic dehydrogenation is preferably conducted at liquid hourly space velocities from about 5 to about 40 hr$^{-1}$ and more preferably from about 10 to about 20 hr$^{-1}$. Especially preferred conditions for the dehydrogenation of $C_{10}$–$C_{14}$ linear paraffins include a temperature from about 800° F. (426° C.) to about 1000° F. (538° C.), a pressure from about 5 psig (34.4 kPa gauge) to about 30 psig (207 kPa gauge), a hydrogen to hydrocarbon mole ratio from about 2 to about 6, and a liquid hourly space velocity from about 10 to about 40 hr$^{-1}$. Such relatively high space velocities conducted in a radial flow catalyst system tends to cause moderate to severe catalyst pinning which prevents or hinders the uniform flow of catalyst into and out of the catalyst bed by gravity flow. The result of pinning is that the high velocity horizontally flowing gases hold the catalyst next to the catalyst-retaining screen which prevents smooth, unimpeded gravity flow of the catalyst particles through the reaction zone. Previously, those practicing hydrocarbon conversion at high space velocities had to deal with the problem of removing catalysts from a catalyst bed by shutting down and reloading the catalyst bed with fresh catalyst or switching to another catalyst bed which has been prepared with fresh catalyst. In modern day hydrocarbon conversion processes, the ability to operate on a continuous basis is a great advantage. Previously, in a high space velocity hydrocarbon conversion process, a swing reactor system was utilized to maintain processing continuity. Since the reactant stream in a hydrocarbon dehydrogenation process is a high temperature vaporous stream moving at a high velocity, the swing reactor system requires additional extensive large diameter piping and valving in order to be able to switch from one catalyst bed to another. The valves utilized in this service are required to be large in diameter, to be able to operate in the open position without unduly restricting flow, to possess the ability to operate at high temperatures and to reliably stop the flow of hot hydrocarbonaceous reactants. These valves are by their very nature expensive and have a tendency to leak and therefore constantly require continuous maintenance for the sake of overall safety and operability. Therefore, in accordance with the present invention the capital cost of a hydrocarbonaceous dehydrogenation process is reduced since there is no longer a need for the piping manifold, block valves, parallel reaction vessel, and an auxiliary preheat furnace needed to preheat the standby reactor before switching it to the processing mode.

In addition to the catalytic dehydrogenation of hydrocarbons, the present invention is particularly useful for catalytic reforming which is also an established and well-known hydrocarbon conversion process in the petroleum refining industry.

In accordance with a preferred embodiment of the present invention, the inlet temperature of the on-line reaction zone containing catalyst is preferably reduced by about 10° F. (5.5° C.) to about 100° F. (55.5° C.) to a second inlet temperature thereby lowering the rate of the hydrocarbon conversion in the reaction zone. After this temperature reduction is initiated, the hydrogen flow is reduced to achieve a hydrogen to hydrocarbon mole ratio which is from about 10% to about 60% of the original hydrogen to hydrocarbon mole ratio and sufficient to unpin said catalyst from the reactor thereby ensuring uniform gravitational catalyst flow through the reactor while maintaining the original mass flow rate of hydrocarbon. Then a quantity of fresh catalyst is introduced into an upper portion of the reaction zone while removing a similar quantity of spent catalyst from a lower portion of the reaction zone. After changing at least a portion of the catalyst in the reaction zone, the hydrogen flow rate is increased and returned essentially to the original flow rate. Subsequently, the inlet temperature of the reaction zone is increased to essentially restore the hydrocarbon conversion to the original level. The reduction in inlet temperature is accomplished by reducing the heat supplied to the combined feed by heat exchangers and/or charge heaters. During the period of reduced hydrocarbon conversion and hydrocarbon flow rate, the product recovery facilities including fractionation may be conveniently "turned down" without the discontinuation of operation which thereby avoids the inconvenience of a complete shutdown. The hydrogen flow rate in this embodiment is preferably reduced without a reduction in the hydrocarbon flow rate. Since the conversion has been reduced by lowering the inlet temperature, the catalyst is protected from premature deactivation that would otherwise occur from the resulting lower hydrogen to hydrocarbon mole ratio.

In accordance with another preferred embodiment of the present invention, the inlet temperature of the on-line reaction zone containing catalyst is preferably reduced by about 10° F. (5.5° C.) to about 100° F. (55.5° C.) to a second inlet temperature thereby lowering the rate of the hydrocarbon conversion in the reaction zone. After this temperature reduction is initiated, the mass flow rate of hydrocarbon is reduced to a second mass flow rate which is sufficient to unpin the catalyst from the reaction zone thereby ensuring uniform gravitational catalyst flow through the reaction zone while maintaining a reduced hydrogen to hydrocarbon mole ratio which is preferably selected from the range of about 10% to about 60% of the hydrogen to hydrocarbon mole ratio utilized prior to instituting the temperature reduction. Then a quantity of fresh catalyst is introduced into an upper portion of the reaction zone while removing a similar quantity of spent catalyst from a lower portion of the reaction zone. After changing at least a portion of the catalyst in the reaction zone, the mass flow rate including the hydrogen flow rate is increased and returned essentially to the original flow rates. Subsequently, the inlet temperature of the reaction zone is increased to essentially restore the hydrocarbon conversion to the original level. The reduction in inlet temperature is accomplished by reducing the heat supplied to the combined feed by heat exchangers and/or charge heaters. During the period of reduced mass flow rate, the product recovery facilities including fractionation may be conveniently "turned down" without the discontinuation of operation which thereby avoids the inconvenience of a complete shutdown. The hydrocarbon flow rate in this embodiment is preferably reduced in tandem with the hydrogen flow rate thereby maintaining a constant recycle hydrogen to hydrocarbon feed rate in order to avoid catalyst damage.

In a commercial size processing unit, we contemplate that the reduced mass flow rate will last for about 2 to 8 hours. Under certain circumstances, the duration of the reduced mass flow rate could be even less. In addition, we contemplate that the removal of a portion of catalyst from the reaction zone would occur, for example, once every week.

As hereinabove described, the annular form catalyst-retaining section is constructed of a top end which is an imperforate screen which prevents the flow of reactants through the upper portion of the catalyst-retaining section. This imperforate upper end defines a portion of the annular-form catalyst-retaining section which is sized to have a volume of greater than about 100% of the volume of the vessel (catalyst loading chamber) which is used to introduce catalyst into the catalyst-retaining section. The purpose of having such an imperforate upper end is to permit the gradual heating of the newly introduced fresh catalyst before this catalyst is contacted with hot hydrocarbonaceous reactant feedstock. This heatup of fresh catalyst in the absence of hydrocarbon reactants is desirable to avoid condensation of the vapor hydrocarbons on cold catalyst. Contact of liquid hydrocarbons with the catalyst during increasing temperature promotes accelerated undesirable coke formation on the catalyst which is manifested by catalyst deactivation. In order to prevent premature contact of the catalyst with hydrocarbon, the imperforate upper end is preferably purged with a hot flowing hydrogen-rich gas stream which may also serve the purpose of heating and reducing the newly introduced catalyst.

The foregoing description clearly illustrates the advantages encompassed by the process of the present invention and the benefits to be afforded with the use thereof.

We claim as our invention:

1. A continuous process for hydrocarbon conversion wherein a hydrocarbon charge stock is catalytically converted in the presence of hydrogen at hydrocarbon conversion conditions including a first inlet temperature, a first hydrogen to hydrocarbon mole ratio and a first mass flow rate of hydrocarbon into a hydrocarbon product stream in a high space velocity moving bed radial flow reactor containing catalyst wherein at least a portion of said catalyst is pinned and thereby immobilized during high space velocity conversion which process comprises:

(a) reducing said first inlet temperature of said reactor by about 10° F. (5.5° C.) to about 100° F. (55.5° C.) to a second inlet temperature thereby lowering the rate of said hydrocarbon conversion;
   (b) reducing said first hydrogen to hydrocarbon mole ratio to a second hydrogen to hydrocarbon mole ratio which is from about 10% to about 60% of said first hydrogen to hydrocarbon mole ratio and sufficient to unpin said catalyst from said reactor thereby ensuring uniform gravitational catalyst flow through said reactor while maintaining said first mass flow rate of hydrocarbon;
   (c) introducing a quantity of fresh catalyst into an upper portion of said reactor while removing a similar quantity of spent catalyst from a lower portion of said reactor;
   (d) increasing said second hydrogen to hydrocarbon mole ratio to essentially said first hydrogen to hydrocarbon mole ratio; and
   (e) increasing said second inlet temperature to essentially restore said hydrocarbon conversion.

2. The process of claim 1 wherein said inlet temperature is reduced by about 18° F. (10° C.) to about 72° F. (40° C.).

3. The process of claim 1 wherein said quantity of fresh catalyst is less than 50% of the catalyst capacity of said reactor.

4. The process of claim 1 wherein said fresh catalyst is new or regenerated catalyst.

5. The process of claim 1 wherein said hydrocarbon conversion comprises dehydrogenation.

6. The process of claim 1 wherein said hydrocarbon conversion comprises reforming.

7. The process of claim 5 wherein said dehydrogenation is conducted at conditions which include a temperature from about 700° F. (371° C.) to about 1400° F. (760° C.), a pressure from subatmospheric to about 50 psig (345 kPa gauge), a hydrogen to hydrocarbon mole ratio from about 0.5 to about 10, and a liquid hourly space velocity from about 5 to about 40 $hr^{-1}$.

8. The process of claim 5 wherein said dehydrogenation is conducted at conditions which include a temperature from about 800° F. (426° C.) to about 1000° F. (538° C.), a pressure from about 5 psig (34.4 kPa gauge) to about 30 psig (207 kPa gauge), a hydrogen to hydrocarbon mole ratio from about 2 to about 6, and a liquid hourly space velocity from about 10 to about 40 $hr^{-1}$.

9. The process of claim 1 wherein said catalyst comprises a platinum group metal component, a tin component, an alkali metal component and a porous carrier material.

10. The process of claim 1 wherein said catalyst comprises a platinum component, a tin component, a lithium component and alumina.

11. The process of claim 1 wherein said fresh catalyst is preheated with hot hydrogen prior to contact with hydrocarbon.

12. A continuous process for hydrocarbon conversion wherein a hydrocarbon charge stock is catalytically converted in the presence of hydrogen at hydrocarbon conversion conditions including a first inlet temperature, a first hydrogen to hydrocarbon mole ratio and a first mass flow rate of hydrocarbon into a hydrocarbon product stream in a high space velocity moving bed radial flow reactor containing catalyst wherein at least a portion of said catalyst is pinned and thereby immobilized during high space velocity conversion which process comprises:

(a) reducing said first inlet temperature of said reactor by about 10° F. (5.5° C.) to about 100° F. (55.5° C.) to a second inlet temperature thereby lowering the rate of said hydrocarbon conversion;
   (b) reducing said first mass flow rate of hydrocarbon to a second mass flow rate of hydrocarbon while maintaining a second hydrogen to hydrocarbon mole ratio from about 10% to about 60% of said first hydrogen to hydrocarbon mole ratio which is sufficient to unpin said catalyst from said reactor thereby ensuring uniform gravitational catalyst flow through said reactor;
   (c) introducing a quantity of fresh catalyst into an upper portion of said reactor while removing a similar quantity of spent catalyst from a lower portion of said reactor;
   (d) increasing said second mass flow rate of hydrocarbon to essentially said first mass flow rate of hydrocarbon;
   (e) increasing said second hydrogen to hydrocarbon mole ratio to essentially said first hydrogen to hydrocarbon mole ratio; and
   (f) increasing said second inlet temperature to essentially restore said hydrocarbon conversion.

13. The process of claim 12 wherein said inlet temperature is reduced by about 18° F. (10° C.) to about 72° F. (40° C.).

14. The process of claim 12 wherein said mass flow rate is reduced by about 10% to about 80%.

15. The process of claim 12 wherein said quantity of fresh catalyst is less than 50% of the catalyst capacity of said reactor.

16. The process of claim 12 wherein said fresh catalyst is new or regenerated catalyst.

17. The process of claim 12 wherein said hydrocarbon conversion comprises dehydrogenation.

18. The process of claim 12 wherein said hydrocarbon conversion comprises reforming.

19. The process of claim 17 wherein said dehydrogenation is conducted at conditions which include a temperature from about 700° F. (371° C.) to about 1400° F. (760° C.), a pressure from subatmospheric to about 50 psig (345 kPa gauge), a hydrogen to hydrocarbon mole ratio from about 0.5 to about 10, and a liquid hourly space velocity from about 5 to about 40 $hr^{-1}$.

20. The process of claim 17 wherein said dehydrogenation is conducted at conditions which include a temperature from about 800° F. (426° C.) to about 1000° F. (538° C.), a pressure from about 5 psig (34.4 kPa gauge) to about 30 psig (207 kPa gauge), a hydrogen to hydrocarbon mole ratio from about 2 to about 6, and a liquid hourly space velocity from about 10 to about 40 hr$^{-1}$.

21. The process of claim 12 wherein said catalyst comprises a platinum group metal component, a tin component, an alkali metal component and a porous carrier material.

22. The process of claim 12 wherein said catalyst comprises a platinum component, a tin component, a lithium component and alumina.

23. The process of claim 12 wherein said fresh catalyst is preheated with hot hydrogen prior to contact with hydrocarbon.

* * * * *